United States Patent [19]
Dulaney

[11] Patent Number: 5,413,761
[45] Date of Patent: May 9, 1995

[54] PERFORATED DIAGNOSTIC DEVICE

[76] Inventor: Dolores P. Dulaney, 369 Wayne Dr., Fairborn, Ohio 45324

[21] Appl. No.: 257,291

[22] Filed: Jun. 9, 1994

[51] Int. Cl.⁶ ............................................. G01N 21/01
[52] U.S. Cl. ........................................ 422/56; 422/58; 422/87; 436/44; 436/46; 436/169; 436/810; 435/4; 435/805
[58] Field of Search ................... 422/56, 58, 61, 87; 436/44, 46, 95, 169, 805, 810; 435/4, 14, 805

[56] References Cited

U.S. PATENT DOCUMENTS

| | | | |
|---|---|---|---|
| 3,920,580 | 11/1975 | Mast | 252/408 |
| 4,275,031 | 6/1981 | Fischer et al. | 422/57 |
| 4,605,629 | 8/1986 | Lang et al. | 436/166 |
| 4,618,475 | 10/1986 | Wang | 422/56 |
| 4,729,959 | 3/1988 | Ryan | 436/14 |
| 4,981,786 | 1/1991 | Dafforn et al. | 435/7 |
| 5,100,619 | 3/1992 | Baker et al. | 422/58 |
| 5,182,191 | 1/1993 | Fan et al. | 435/7.9 |
| 5,183,742 | 2/1993 | Omoto et al. | 435/14 |
| 5,187,100 | 2/1993 | Matzinger et al. | 436/16 |
| 5,209,904 | 5/1993 | Forney et al. | 422/73 |
| 5,212,065 | 5/1993 | Pegg et al. | 435/7.9 |

FOREIGN PATENT DOCUMENTS 0369836  5/1990  European Pat. Off. .
2026160  1/1980  United Kingdom .

Primary Examiner—David A. Redding
Attorney, Agent, or Firm—Richard Litman

[57] ABSTRACT

A diagnostic device in the form of a blood glucose monitoring strip of the dip-and-read variety, and which has a first, outer test area which is chemically identical with a second, interior test area. A blood sample is tested in the first area. The first area is torn off and discarded. Then, another, similar test is conducted employing the remaining, second, interior test area. A line of perforation divides the first and second areas. Notches may be defined in the outer ends of both test areas to facilitate reading of the blood impregnated samples with the use of a suitable photometric machine, for example.

7 Claims, 1 Drawing Sheet

PERFORATED DIAGNOSTIC DEVICE

BACKGROUND OF THE INVENTION

1. FIELD OF THE INVENTION

The present invention relates to diagnostic devices and, more particularly, to an improved test strip for blood glucose monitoring.

2. DESCRIPTION OF THE PRIOR ART

Blood glucose monitoring strips are known. Usually, such strips include an end grasped by the fingers and a single testing area at an opposite end, onto which a sample of blood is deposited, followed by a determination of the glucose level in the sample. Such prior art monitoring strips include but one testing area; if further testing is indicated, e.g., for confirmation purposes, then another entire monitoring strip must be used. This is both inconvenient and expensive.

The instant invention solves the problem by providing a blood glucose monitoring strip having at least two, serially arranged testing areas, divided conveniently by a tear off perforation line, for example, so that a subsequent test may be conducted without the need of acquiring an entire new monitoring strip. This arrangement provides numerous advantages as will be discussed in detail below.

Dry dip-and-read reagent strips for use in determining the concentration of glucose are, of course, well known. Continuous and accurate monitoring of the level of glucose in the blood is extremely important in the management of diabetes. Insulin and the amount of carbohydrate ingested control the level of glucose in the blood. If there is too little insulin present, the result is a very high glucose level. Conversely, if there is too much insulin present, then the glucose level will be unacceptably low. Either condition presents serious health consequences for the diabetic.

Furthermore, it is preferable to determine glucose levels directly from a blood sample rather than a urine sample. Urine glucose measurements are useful, but do not accurately confirm the level of glucose in the blood, because a urine glucose level is related directly to the level of glucose in the blood and the ability of the kidney to reabsorb glucose. So, in point of fact, a urine sample cannot tell a diabetic how low his glucose level is.

Commonly, the monitoring strips under discussion include a plastic strip with an absorbent paper piece impregnated with an enzyme system as well as a color indicator compound which changes color when oxidized. After the sample being tested is deposited onto the strip, the color formed on the strip is either machine read or compared with a color chart which is calibrated to represent various glucose concentrations. Several brands of such strips are available, including: the Lifescan strip, manufactured by Lifescan, Inc., Mountain View, Calif.; the Chemstrip bG strip, a trademarked product of Bio-Dynamic/Boehringer Mannheim Diagnostics, Inc.; and a strip sold under the trademark Dextrostix by Ames Company Division, Miles Laboratories, Inc. Further discussion of such strips can be found in the following enumerated patents, although these specific patents are directed to control solutions for such strips. These patents are: U.S. Pat. No. 3,920,580, issued Nov. 18, 1975 to Raymond L. Mast, and assigned to Miles Laboratories, Inc., Elkhart, Ind.; U.S. Pat. No. 4,729,959, issued Mar. 8, 1988 to Wayne L. Ryan, and assigned to Streck Laboratories, Inc. of Omaha, Nebr.; and U.S. Pat. No. 5,187,100, issued Feb. 16, 1993 to David P. Matzinger et al., and assigned to Lifescan, Inc., of Mountain View, Calif. This last mentioned patent will be discussed again hereinbelow.

There are other prior art teachings directed to testing strips or the like and including more than one testing area, but in each instance, the additional testing area or areas are provided for different tests or readings, and are employed simultaneously in conducting a test, rather than serially. For example, U.S. Pat. No. 4,275,031 issued Jun. 23, 1981 to Wolfgang Fischer et al., and assigned to Merck Patent Gesellschaft mit beschrankter Haftung of Darmstadt, Germany, shows a strip used in carrying out colorimetric or photometric determinations, and including spaced apart testing areas or reagent zones arranged one above another. However, these multiple zones are provided so that multiple analyses may be conducted simultaneously, rather than serially, the zones being identical so that the same test is again conducted, as is the case with the instant invention.

Similarly, the following six prior patent and published patent applications show testing devices with multiple zones or areas which are different from one another so that different analyses may be conducted simultaneously. None of these prior teachings is directed to testing strips with serially arranged, identical testing areas or zones for serially conducting precisely the same test, e.g., blood glucose determination. U.S. Pat. No. 5,183,742, issued Feb. 2, 1993 to Kouichi Omoto, et al., and assigned to Dai Nippon Insatsu Kabushiki of Kaisha, Japan teaches a testing device or strip having multiple, side by side or vertically arrayed detection regions or zones, but for simultaneous testing of a body fluid, so as to determine, for example, levels of glucose and protein and the pH of a sample. Another test device for the determination of glucose, the device including a strip with serially arranged zones, these being a measurement zone, a reaction zone, and a detection zone, is seen in U.K. Patent Application 2,026,160, published Jan. 30, 1980, and filed by VEB Arzneimittelwerk of Dresden, Germany. Again, the two disclosures just mentioned specifically teach a strip having different zones with different characteristics for the simultaneous testing of a sample, rather than serial testing of a sample with a strip having chemically identical testing zones or areas but employed serially, one after the other.

U.S. Pat. No. 4,981,786, issued Jan. 1, 1991 to Geoffrey A. Daffom et al., and assigned to Syntex (U.S.A.) Inc., of Palo Alto, California teaches a multiple port assay device wherein a sample is introduced through a first port to a liquid absorbing zone, and a liquid reagent other than the sample is introduced through a second port to the liquid absorbing zone. Again, serial, identical testing employing a strip with chemically identical testing zones is not taught or suggested.

The following two patent are directed to fecal occult blood specimens and assay techniques. Each discloses a sampling device with at least two fecal matter smear areas for receiving a sample; serial testing with chemically identical areas is neither taught or suggested. The two patent are U.S. Patent No's. 5,100,619, issued Mar. 31, 1992 to Josefina T. Baker et al., and assigned to Beckman Instruments, Inc., of Fullerton, Calif., and U.S. Pat. No. 5,182,191, issued Jan. 26, 1993, to Eugene Fan et al., and assigned to Pacific Biotech, Inc., of San Diego, Calif.

Published European patent application No. 0 369 836, filed by Institut Textile de France and published May 23, 1990, teaches yet another testing device with multiple test areas or zones for conducting different tests on the same sample. Again, the structure and use of a strip having chemically identical zones for serial testing is not seen in this reference.

Accordingly, none of the above inventions and patents, taken either singly or in combination, is seen to describe the instant invention as claimed.

SUMMARY OF THE INVENTION

The present invention is directed to a blood glucose monitoring strip having at least two chemically identical testing areas or zones which are divided by a convenient perforation line so that an outer zone may be employed for a glucose level determination test and discarded, followed by the use of the second zone or area for a later but identical test. The two zone strip may be dimensioned and configured so that a first, outer test end may simply be folded or turned under the second so that the same packaging that is employed with such strips currently may be used to package and distribute the instant invention. Costs savings are manifestly obvious. Glucose testing/monitoring whether in the home or in an institution is performed at least once daily and often two or three times daily. Thus, substantial savings are realized with the instant invention since at least two tests can be performed with the same strip having two, serially arranged areas or zones, used sequentially.

Furthermore, in an institutional setting, often the caretaker will bring only one strip into a patient's or resident's room for testing blood glucose. If a "HIGH" reading is the result or if an insignificant amount of blood is used, then the caretaker must go to a main medication area or station to acquire another strip for further testing. This is both time consuming and cost inefficient.

When the instant invention is used in an institutional setting, each individual patient or resident may have an individual container, for which they may be charged an appropriate amount. Later, the patient or resident may take home the remaining test strips for continued monitoring of blood glucose.

Currently available blood glucose monitoring strips range in price from $30.00 to $35.00 for fifty strips, and the life date of such a supply is approximately one year. By producing strips in accordance with the instant invention, each strip having two, chemically identical areas or zones arranged serially on the same strip, so that identical glucose monitoring tests may be run sequentially without need of an additional strip, almost a double quantity of tests may be run with only a slight increase in cost when compared with available single strips, since the identical packaging is employed with the instant invention and the additional test area is simply a reduced length, easily torn off segment at the outer end of the strip.

Accordingly, it is a principal object of the invention to provide a blood glucose monitoring strip in the form of a perforated diagnostic device with two chemically identical testing zones, and of uncomplicated structure, having an outer, first, tear-off testing end which is discarded after use, whereupon the second zone is employed for a blood glucose test.

It is another object of the invention to provide a blood glucose monitoring strip structured to conduct two separate, sequential tests, which strip may be conveniently folded to fit within the same exact packaging employed for currently available, single test strip.

It is a further object of the invention to provide a perforated diagnostic device with a shorter, first, outer tear-off test end which, after use and discarding the outer end, is employed to conduct an identical test using the remaining, longer portion of the strip.

Still another object of the invention is to provide a method of blood glucose monitoring wherein a strip having two chemically identical zones is used to conduct a first test with an outer end of the strip, followed by a second, later but identical test using another segment of the strip, thus to monitor blood glucose levels sequentially with a single, two zoned testing strip.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT(s)

Figure 1:
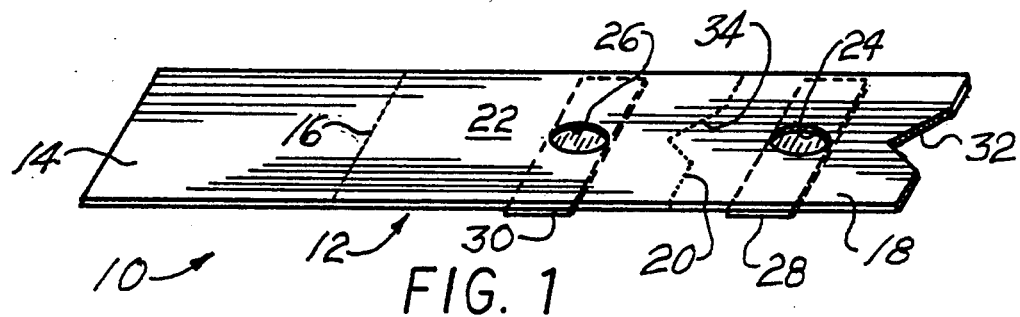
FIG. 1 is a perspective view of a test strip according to a preferred embodiment of the present invention.
Figure 2:
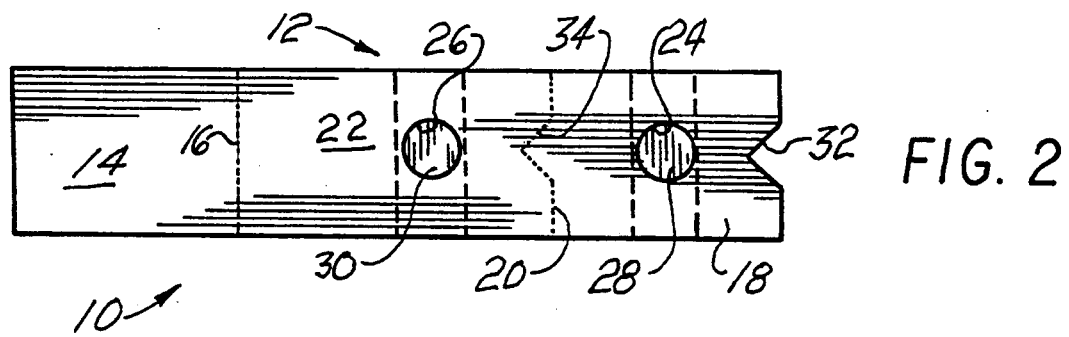
FIG. 2 is a top, plan view thereof.
Figure 3:
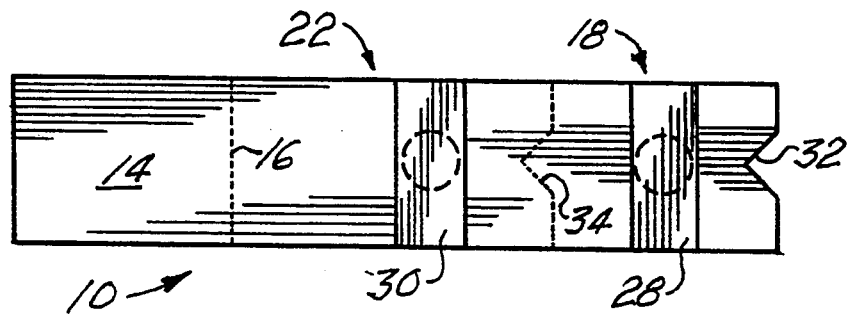
FIG. 3 is a bottom, plan view thereof.
Figure 4:
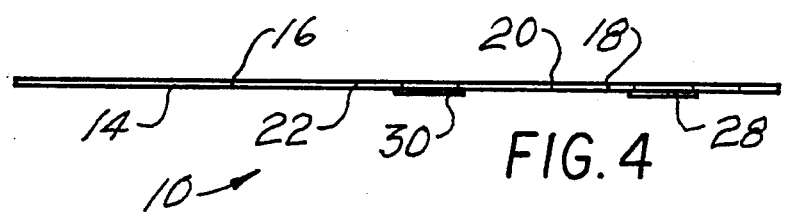
FIG. 4 is a side elevational view thereof.

The present invention is an improved test strip 10 for blood glucose monitoring, and which includes a main, structural spine 12 of plastic or other suitable material. The strip 10 includes a first end 14 configured for grasping by the fingers of a user. The graspable end 14 is demarcated by a line 16 in the several views.

An outer, first testing area or zone is indicated at 18. This zone 18 is connected by a line of perforation 20 to a second, interior testing area or zone 22. Further, each zone 18, 22, includes a central blood sample deposition orifice 24, 26, beneath which is located a layer of absorbent, impregnated paper 28, 30, respectively. A leading edge of each zone 18, 22, may be identically notched as at 32, 34, respectively. These notches are provided so that the test zones or areas may be accurately aligned with a photometric machine (not shown), known in the art and employed to determine the presence of glucose in a sample of blood.

Figure 5:
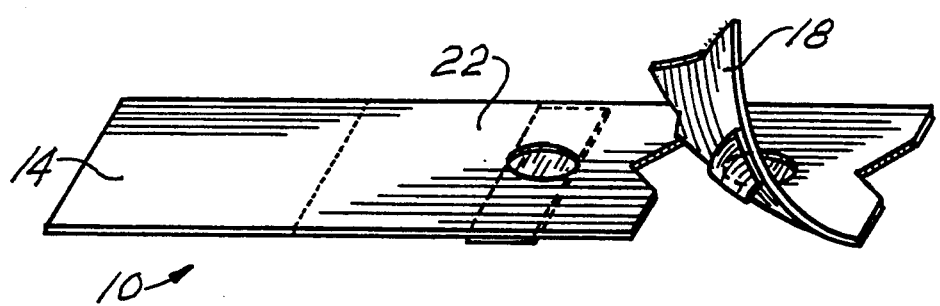
FIG. 5 is a perspective view similar to FIG. 1, but, showing separation of a first test zone or segment from a second zone, along a line of perforation.

The construction of the strip with the use of sample deposition orifices and absorbent paper therebeneath forms no part of the instant invention per se, and is rather adequately described in the Lifescan patent, U.S. Pat. No. 5,187,100 issued Feb. 16, 1993 to David P. Matzinger et al., discussed above and incorporated herein by reference. The point is that each testing area or zone 18, 22 is chemically identical so that sequential tests may be conducted on sequential blood samples, with the same strip 10, the first strip zone 18 being torn from the second zone 22 and discarded, after use, and as is shown in FIG. 5. Thus, sequential, identical tests may be conducted with two different but chemically identical zones of the same strip.

Thus, in use, a first blood glucose test is run, using the first zone 18. Thereafter, the first zone 18 is torn from the second, and a subsequent test is run employing the chemically identical, second zone or area 22.

It is to be understood that the present invention is not limited to the sole embodiment described above, but encompasses any and all embodiments within the scope of the following claims.

I claim:

1. A diagnostic strip device for testing for the presence of predetermined constituents in more than one sample of body fluids, comprising:
   a spine making up the major portion of said diagnostic device, said spine having a first end and a second, outer end, said spine having a longitudinal axis passing through said first end, and said second, outer end;
   a finger grasping portion defined at said first end;
   a first testing zone located along said longitudinal axis of said spine at said second outer end, said first testing zone having predetermined chemical constituents for the testing of the presence of predetermined constituents in a sample of body fluid;
   a second testing zone located along said longitudinal axis of said spine and adjoining said first testing zone and having a predetermined chemical constituents identical to those of said first testing zone, for the testing of the presence of predetermined constituents in another sample of body fluid; and
   means defining a line of separation between said first and second zones, said means defining a line of separation bisecting said longitudinal axis of said spine, whereby after use of said first zone, the same may be separated from said second zone, whereupon a second test may be conducted with the use of said second zone and another sample of body fluid.

2. The invention as defined in claim 1, wherein said line of separation comprises means defining a line of perforation between said first and second zones, whereby said first zone may be torn from said second zone.

3. The invention as defined in claim 1, wherein said first and second zones are of identical widths, said first zone having a predetermined length shorter than the length of said second zone.

4. The invention as defined in claim 1 wherein each of said zones include absorbent paper means for receiving a sample of body fluid.

5. The invention as defined in claim 4 wherein each zone further comprises means defining a sample receiving orifice therethrough, said absorbent paper means being located beneath said orifice.

6. The invention as defined in claim 1, wherein said first test zone further comprises a notch formed in an edge thereof, and wherein said second test zone further comprises a notch formed in an area selected from the group consisting of an edge thereof and along said means defining a line of separation between said first and second zones.

7. A method of serially testing and monitoring blood glucose levels comprising the steps of:
   a. providing a testing strip having side by side arranged, outer and inner, chemically identical testing areas therewithin;
   b. depositing a first blood sample on the outer test area and determining the amount of glucose therein;
   c. separating the outer test area from the inner test area and discarding the same; and
   d. conducting a second, separate blood glucose level test by depositing another blood sample on the inner test area and determining the amount of glucose therein.

* * * * *